United States Patent [19]
Vora et al.

[11] Patent Number: 6,049,017
[45] Date of Patent: Apr. 11, 2000

[54] ENHANCED LIGHT OLEFIN PRODUCTION

[75] Inventors: Bipin V. Vora, Darien; Terry L. Marker, Warrenville; Paul T. Barger, Arlington Heights, all of Ill.

[73] Assignee: UOP LLC, Des Plaines, Ill.

[21] Appl. No.: 09/059,906

[22] Filed: Apr. 13, 1998

[51] Int. Cl.[7] .............................. C07C 1/00; C07C 1/20; C07C 4/06
[52] U.S. Cl. .................. 585/324; 585/329; 585/638; 585/639; 585/640
[58] Field of Search ...................................... 585/638, 639, 585/640, 324, 329

[56] References Cited

U.S. PATENT DOCUMENTS

| | | | |
|---|---|---|---|
| 3,928,483 | 12/1975 | Chang et al. | 260/668 R |
| 4,025,575 | 5/1977 | Chang et al. | 260/682 |
| 4,252,479 | 2/1981 | Scherfenberg | 406/182 |
| 4,447,669 | 5/1984 | Hamon et al. | 585/640 |
| 4,499,314 | 2/1985 | Seddon et al. | 585/408 |
| 4,527,001 | 7/1985 | Kaiser | 585/643 |
| 4,861,938 | 8/1989 | Lewis et al. | 585/640 |
| 4,973,792 | 11/1990 | Lewis et al. | 585/638 |
| 5,026,935 | 6/1991 | Leyshon et al. | 585/315 |
| 5,026,936 | 6/1991 | Leyshon et al. | 585/315 |
| 5,043,522 | 8/1991 | Leyshon et al. | 585/651 |
| 5,095,163 | 3/1992 | Barger | 585/640 |
| 5,126,308 | 6/1992 | Barger et al. | 502/214 |
| 5,191,141 | 3/1993 | Barger et al. | 585/640 |
| 5,475,183 | 12/1995 | Araki et al. | 585/640 |
| 5,523,502 | 6/1996 | Rubin | 585/324 |
| 5,714,662 | 2/1998 | Vora et al. | 585/640 |
| 5,744,680 | 4/1998 | Mulvaney, III et al. | 585/640 |
| 5,817,906 | 10/1998 | Marker et al. | 585/640 |
| 5,912,393 | 6/1999 | Barger et al. | 585/640 |

FOREIGN PATENT DOCUMENTS

| | | |
|---|---|---|
| 0 109 059 B1 | 10/1983 | European Pat. Off. . |
| 0 109 060 B1 | 10/1983 | European Pat. Off. . |

OTHER PUBLICATIONS

Kaiser, V. and Piciotti, M., "Better Ethylene Separation Unit" *Hydrocarbon Processing Magazine*, Nov. 1988, 00. 57–61.

*Primary Examiner*—Walter D. Griffin
*Attorney, Agent, or Firm*—Thomas K. McBride; John G. Tolomei; Richard P. Silverman

[57] ABSTRACT

A process is disclosed for enhancing the production of light olefins with a catalytic reaction zone containing small pore zeolitic and non-zeolitic catalysts which can significantly improve the yield of ethylene and propylene in a process for the conversion of light olefins having four carbon atoms per molecule and heavier. Specifically, a $C_4$ olefin stream from an ethylene production complex is converted in a reaction zone over a non-zeolitic catalyst at effective conditions to produce a product mixture containing ethylene and propylene. Ethylene and propylene are separated from the product mixture and recovered. A portion of the remaining heavy hydrocarbons and paraffins may be recycled to the reaction zone for further conversion, or oligomerized to produce valuable downstream products. The additional step of removing iso-olefins from the recycle stream provided significant advantages. The process of the present invention may be applied in commercial ethylene plants, in petroleum refining catalytic cracking operations, and in processes for the conversion of oxygenates such as methanol-to-olefins to enhance the production of ethylene and propylene.

25 Claims, 1 Drawing Sheet

ENHANCED LIGHT OLEFIN PRODUCTION

FIELD OF THE INVENTION

The present invention relates to an improved method for the production of ethylene and propylene from a heavier olefin feedstock.

BACKGROUND OF THE INVENTION

Ethylene, a light olefin hydrocarbon with two carbon atoms per molecule, is an important building block petrochemical. The primary use for ethylene is as a monomer for the production of polyethylene for both linear low density polyethylene and high density polyethylene. Other uses include the production of vinyl chloride, ethylene oxide, ethylbenzene and alcohols. Essentially all of the ethylene is produced by the steam cracking or pyrolysis of hydrocarbons. Hydrocarbons used as feedstock for ethylene plants include natural gas, naphtha, and gas oils. The natural gas components are generally paraffinic and include ethane, propane, and butane. Ethylene is co-produced with propylene and butylenes. Depending upon the feedstock, the products of commercial ethylene plants can include higher olefinic and aromatic hydrocarbons with more than 4 atoms per molecule.

An ethylene plant is a very complex combination of reaction and gas recovery systems. The feedstock is charged to a cracking zone in the presence of steam at effective thermal conditions to produce a pyrolysis reactor effluent gas mixture. The pyrolysis reactor effluent gas mixture is stabilized and separated into purified components through a sequence of cryogenic and conventional fractionation steps. A typical ethylene separation section of an ethylene plant containing both cryogenic and conventional fractionation steps to recover an ethylene product with a purity exceeding 99.5% ethylene is described in an article by V. Kaiser and M. Picciotti, entitled, "Better Ethylene Separation Unit." The article appeared in HYDROCARBON PROCESSING MAGAZINE, November 1988, pages 57–61 and is hereby incorporated by reference.

Methods are known for increasing the conversion of portions of the products of the ethylene production from a zeolitic cracking process to produce more ethylene and propylene by a disproportionation or metathesis of olefins. Such processes are disclosed in U.S. Pat. Nos. 5,026,935 and 5,026,936 wherein a metathesis reaction step is employed in combination with a catalytic cracking step to produce more ethylene and propylene by the metathesis of $C_4$ and heavier molecules. The catalytic cracking step employs a zeolitic catalyst to convert a hydrocarbon stream having 4 or more carbon atoms per molecule to produce olefins having fewer carbon atoms per molecule. The hydrocarbon feedstream to the zeolitic catalyst typically contains a mixture of 40 to 95 wt-% paraffins having 4 or more carbon atoms per molecule and 5 to 60 wt-% olefins having 4 or more carbon atoms per molecule. In U.S. Pat. No. 5,043,522, it is disclosed that the preferred catalyst for such a zeolitic cracking process selected from acid zeolites of the ZSM type and borosilicates. Of the ZSM-type catalysts, ZSM-5 was preferred. It was disclosed that other zeolites containing materials which could be used in the cracking process to produce ethylene and propylene included zeolite A, zeolite X, zeolite Y, zeolite ZK-5, zeolite ZK-4. synthetic mordenite, dealuminized mordenite, as well as naturally occurring zeolites including chabazite, faujasite, mordenite, and the like. Zeolites which were ion-exchanged to replace alkali metal present in the zeolite were preferred. Preferred cation exchange cations were hydrogen, ammonium, rare earth metals and mixtures thereof.

European Patent No. 109,059B1 discloses a process for the conversion of a feedstream containing olefins having 4 to 12 carbon atoms per molecule into propylene by contacting the feedstream with a ZSM-5 or a ZSM-11 zeolite having a silica to alumina molar ratio less than or equal to 300 at a temperature from 400 to 600° C. The ZSM-5 or ZSM-1 1 zeolite is exchanged with a hydrogen or an ammonium cation. The reference also discloses that, although the conversion to propylene is enhanced by the recycle of any olefins with less than 4 carbon atoms per molecule, paraffins which do not react tend to build up in the recycle stream. The reference provides an additional oligomerization step wherein the olefins having carbon atoms less than 4 are oligomerized to facilitate the removal of paraffins such as butane and particularly isobutane which is difficult to separate from $C_4$ olefins by conventional fractionation. In a related European Patent 109060B1, a process is disclosed for the conversion of butenes to propylene. The process comprises contacting butenes with a zeolitic compound selected from the group consisting of silicalites, boralites, chromosilicates and those zeolites ZSM-5 and ZSM-11 in which the mole ratio of silica to alumina is greater than or equal to 350. The conversion is carried out at a temperature from 500 to 600° C. and at a space velocity of from 5 to 200 kg/hr of butenes per kg of pure zeolitic compound. The European Patent 109060B1 discloses that silicalite-1 is an ion-exchanged, impregnated, or co-precipitated form with a modifying element selected from the group consisting of chromium, magnesium, calcium, strontium and barium.

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. Nos. 3,928,483, 4,025,575, 4,252,479 (Chang et al.); 4,496,786 (Santilli et al.); 4,547,616 (Avidan et al.); 4,677,243 (Kaiser); 4,843,183 (Inui); 4,499,314 (Seddon et al.); 4,447,669 (Harmon et al.); 5,095,163 (Barger); 5,191,141 (Barger); 5,126,308 (Barger); 4,973,792 (Lewis); and 4,861,938 (Lewis).

Generally, the heavier olefins having six or more carbon atoms per molecule which are produced in commercial ethylene plants are useful for the production of aromatic hydrocarbons. Portions of the olefin product include olefins with four carbon atoms per molecule. This portion includes both mono-olefins and di-olefins and some paraffins, including butane and iso-butane. Because the portion with four carbon atoms per molecule is generally less valuable and requires significant processing to separate di-olefins from the mono-olefins, processes are sought to improve the utilization of this portion of the ethylene plant product and enhancing the overall yield of ethylene and propylene.

SAPO catalysts are often employed in the conversion of oxygenates into light olefins, particularly light olefins having less than four carbon atoms per molecule. In such processes, the ratio of ethylene to propylene produced on a carbon basis varies from about 0.1 to about ten, and more typically, the ratio of ethylene to propylene ranges from about 0.8 to about 2.5. Methods are sought to alter the product distribution from the oxygenate conversion process for making light olefins to overcome equilibrium limitations of the SAPO catalyst. These and other disadvantages of the prior art are overcome by the present invention, and a new improved process for conversion of oxygenates to hydrocarbons, specifically olefinic hydrocarbons, is provided.

It is an objective of the present invention to provide a commercial process for enhancing the production of ethylene and propylene from the catalytic conversion of butene and heavier olefins.

It is an objective of the present invention to provide a process for increasing the production of ethylene and propylene in a methanol-to-olefin facility by the further conversion of butene and heavier olefins.

It is an objective to provide an economic route for enhancing the production of ethylene and propylene from a catalytic cracking operation in a petroleum refinery.

SUMMARY OF THE INVENTION

In the present invention, a novel use has been discovered for a group of small pore zeolitic and non-zeolitic catalysts which can significantly improve the yield of ethylene and propylene in a process for the conversion of light olefins having four carbon atoms per molecule and heavier. Specifically, in accordance with the invention, a $C_4$ plus olefin stream from an ethylene production complex is converted in a reaction zone over a selective catalyst at effective conditions to produce a product mixture containing ethylene and propylene. Ethylene and propylene are separated from the product mixture and recovered. A portion of the remaining heavy hydrocarbons ($C_4$ plus olefins) and paraffins may be recycled to the reaction zone for further conversion, or oligomerized to produce valuable downstream products. The process of the present invention may be applied in commercial ethylene plants, in petroleum refining catalytic cracking operations, and in processes for the conversion of oxygenates such as methanol-to-olefins. One aspect of the present invention is a process step which removes a relatively low yielding component of the butene stream, iso-butylene, which it was surprisingly discovered was not converted to the same degree as linear mono-olefins and thus reduced the effectiveness of the overall process. A processing step for the selective removal of the iso-olefins provided the additional benefit of the simultaneous production of high value byproducts. The iso-olefin removal step reduced the size of the butene conversion zone and improved the overall value of the products from the process of the invention.

In one embodiment, the invention is a process for producing ethylene and propylene. The process comprises a series of steps. A feedstream is passed to an olefin production zone and therein an olefinic product stream comprising ethylene, propylene, and butylene and heavier olefins is produced. The olefinic product stream is passed to an olefin separation zone to provide an ethylene product stream, a propylene product stream, a mixed butylene and heavier stream, and a reject stream. The mixed butylene and heavier stream comprising mono-olefins, such as normal and iso-olefins, paraffins, and di-olefins is passed to a di-olefin removal zone to provide a mono-olefin stream comprising normal olefins, iso-olefins, and paraffins. At least a portion of the mono-olefin stream is converted in an olefin conversion zone containing an acid catalyst selective for the conversion of iso-olefins in the presence of at least a stoichiometric amount of an oxygen-containing compound to provide a conversion product stream comprising oxygenates, normal olefins, and paraffins. The conversion product stream is passed to an oxygenate separation zone to separate oxygenates from the normal olefins and produce a net butylene stream. At least a portion of the net butylene stream is passed to a butylene cracking zone and therein the net butylene stream is contacted with a small pore selective catalyst for the cracking of the normal olefins to produce a light olefin stream comprising additional amounts of ethylene and propylene which are recovered.

In another embodiment, the invention is a process for producing ethylene and propylene. The process comprises a series of steps. A feedstream comprising an oxygenate selected from the group consisting of methanol, dimethyl ether, ethanol, and mixtures thereof is passed to an olefin production zone containing a non-zeolitic catalyst. The non-zeolitic catalyst has an effective small pore size and an empirical chemical composition, on an anhydrous basis, which is expressed by the empirical formula:

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. An olefinic product stream comprising ethylene, propylene, and butylene and heavier olefins is produced in the olefin production zone. The olefinic product stream is passed to an olefin separation zone to provide an ethylene product stream, a propylene product stream, a mixed butylene and heavier stream, and a reject stream. The mixed butylene and heavier stream comprising mono-olefins and di-olefins is passed to a selective hydrogenation zone and therein the mixed butylene and heavier stream is contacted with a hydrogenation catalyst in the presence of hydrogen convert the di-olefins to mono- olefins to provide a mixed mono-olefin stream comprising normal olefins, iso-olefins, and paraffins. The mixed mono-olefin stream is passed to an etherification zone containing an acid catalyst, and in the presence of at least a stoichiometric amount of an alcohol, the iso-olefins are converted to provide an ether product stream essentially free of iso-olefins comprising oxygenates, normal olefins, and paraffins. The ether product stream is passed to an oxygenate separation zone to separate oxygenates from the normal olefins and produce a net butylene stream. At least a portion of the net butylene stream at effective cracking conditions is passed to a butylene cracking zone containing a small pore catalyst selective for the conversion of linear mono-olefins to light olefins and therein the net butylene stream is contacted with the small pore catalyst to produce a light olefin stream comprising additional amounts of ethylene and propylene. The additional amounts of ethylene and propylene are recovered.

BRIEF DESCRIPTION OF THE DRAWING

The figure is a schematic block flow diagram of the process of the present invention.

DETAILED DESCRIPTION OF THE INVENTION

Figure 1:
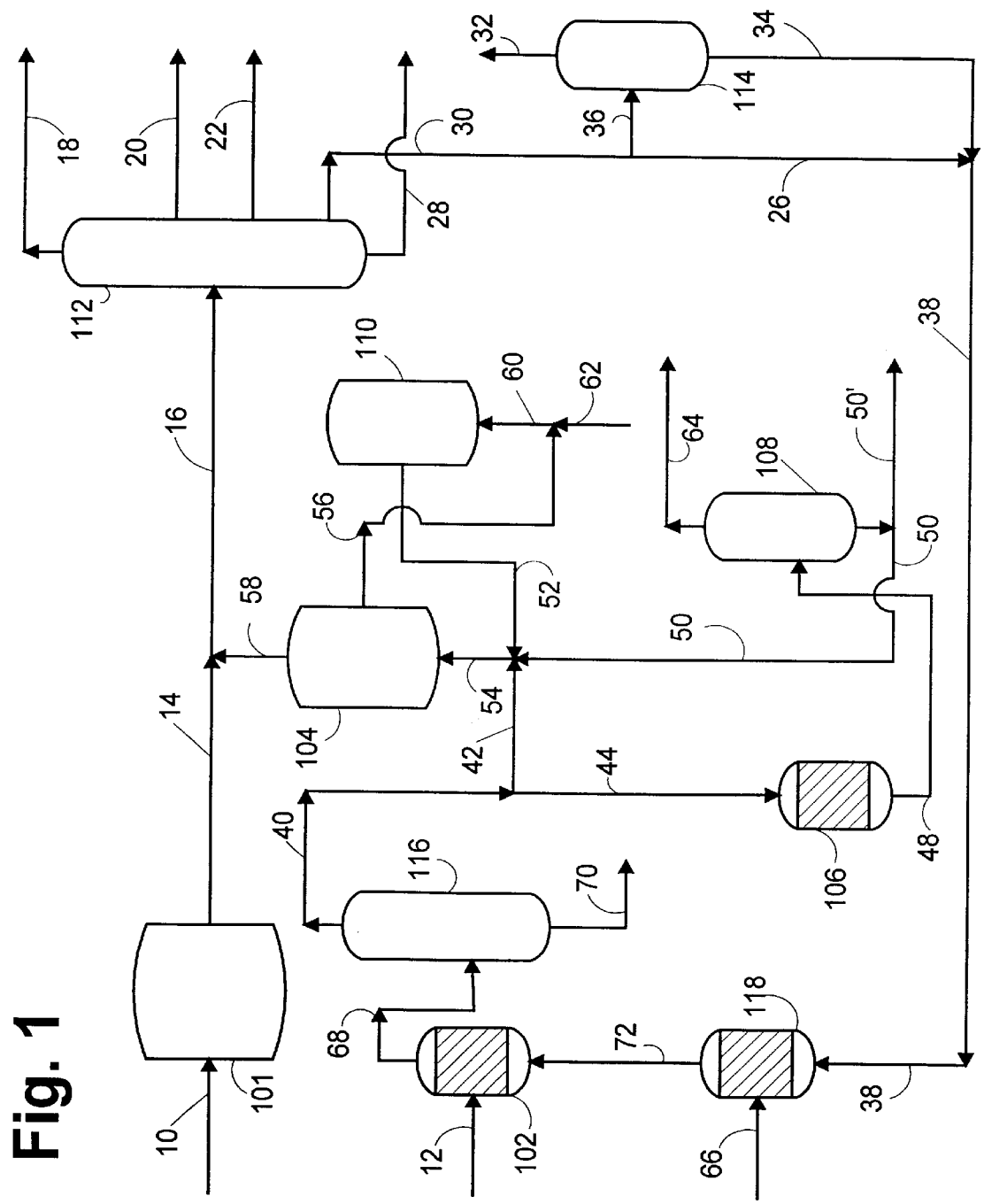

The feedstream of the present invention may be derived from steam cracking, the catalytic cracking of petroleum gas oils, or the conversion of oxygenates to olefins. In the steam cracking of hydrocarbons such as ethane, liquefied petroleum gas, naphtha, and gasoil, a steam cracking product is produced which comprises olefins such as ethylene, propylene, butylene, and heavier hydrocarbons. The composition of the heavier hydrocarbons from the stream cracking process will vary according to the feedstock charged to the steam cracking reaction zone. The lighter the feedstock, the more light olefins are produced. As the steam cracking feedstock increases in carbon number, the more aromatics are formed among the heavier hydrocarbons. Generally, the $C_4$ fraction, produced by the steam cracking reaction may contain as much as 45 weight percent di-olefins as butadiene, and about 50 to about 60 weight percent mono-olefins such as normal butenes and iso-butenes. Approximately 15 to about 25 weight percent of the $C_4$ fraction comprises iso-butylene. In fluid catalytic cracking of petroleum gas oils, the $C_4$ fraction comprises between 40 and about 60 percent olefins, including both mono-olefins and di-olefins. Paraffins in the product include isobutane, isopentane, normal pentane, as well as propane and n-butane. The mono-olefms include butene-1, butene-2, iso-butene, 2-methyl-2-butene, 2-methyl-1-butene, 3-methyl-1-butene, 1-pentene, 2-pentene, cyclopentene and propylene. The hydrocarbon feedstream may also contain di-olefins such as 1,3-butadiene and 1,3-pentadiene. Approximately 0.5 to about 1 weight percent of the $C_4$ components comprise butadiene, and about 15 to about 20 percent of the $C_4$ components from a fluid catalytic cracking process comprise iso-butylene, about 30 weight percent of the $C_4$ fraction comprise normal butenes - such as butene-1 and butene-2, and the balance are paraffins. In the conversion of oxygenates such as methanol to olefins, the $C_4$ fraction less than about 1 weight percent butadiene, and less than about 5 weight percent paraffins. Preferably, the $C_4$ fraction from a methanol-to-olefins reaction zone comprises less than about 20 weight percent iso-butene, and more preferably, the $C_4$ fraction from a methanol-to-olefins reaction zone comprises less than about 15 weight percent iso-butene. A $C_4$ plus olefin fraction comprises the components of the $C_4$ fraction as well as $C_5$, $C_6$ and heavier olefins.

Central to the process of the present invention is a catalytic process for the cracking of butenes to produce additional amounts of ethylene and propylene. The butene cracking reaction zone contains a small pore size catalyst. The preferred small pore catalysts are defined as having pores at least a portion, preferably a major portion, of which have an average effective diameter characterized such that the adsorption capacity (as measured by the standard McBain-Bakkr gravimetric adsorption method using given adsorbate molecules) shows adsorption of oxygen (average kinetic diameter of about 0.346 nm) and negligible adsorption of isobutane (average kinetic diameter of about 0.5 nm). More preferably, the average effective diameter is characterized by adsorption of xenon (average kinetic diameter of about 0.4 nm) and negligible adsorption of isobutane, and most preferably, by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Angstroms. The average effective diameter of the pores of preferred catalysts is determined by measurements described in D. W. Breck, *ZEOLITE MOLECULAR SIEVES* by John Wiley & Sons, New York (1974), hereby incorporated by reference in its entirety. The term "effective diameter" is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves, and non-zeolitic molecular sieves.

Zeolitic molecular sieves in the calcined form may be represented by the general formula:

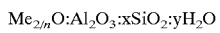

where Me is a cation, x has a value from about 2 to infinity, n is the cation valence and y has a value of from about 2 to 10.

Non-zeolitic molecular sieves include molecular sieves which have the proper effective pore size and are embraced by an empirical chemical composition, on an anhydrous basis, expressed by the empirical formula:

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the element mixture present. Preferred elements (EL) are silicon, magnesium and cobalt with silicon being especially preferred.

The preparation of various ELAPOs are well known in the art and may be found in U.S. Pat. Nos. 5,191,141 (ELAPO); 4,554,143 (FeAPO); 4,440,871 (SAPO); 4,853,197 (MAPO, MnAPO, ZNAPO, CoAPO); 4,793,984 (CAPO), 4,752,651 and 4,310,440; all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, preferred sources include fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

A preferred embodiment of the invention is one in which the element (EL) content varies from about 0.005 to about 0.05 mole fraction. If EL is more than one element, then the total concentration of all the elements is between about 0.005 and 0.05 mole fraction. An especially preferred embodiment is one in which EL is silicon (usually referred to as SAPO). The SAPOs which can be used in the instant invention are any of those described in U.S. Pat. Nos. 4,440,871; 5,126,308, and 5,191,141. SAPO catalysts which are suitable for the present invention include SAPO-11, SAPO-17, and SAPO-34. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å.

Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 Å and less than about 5.0 Å.

The preferred oxygenate conversion catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are often, to some extent, porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like.

If matrix materials, e.g., binder and/or filler materials, are included in the catalyst composition, the non-zeolitic and/or zeolitic molecular sieves preferably comprise about 1% to 99%, more preferably about 5% to about 90%, and still more preferably about 10% to about 80% by weight of the total composition. The preparation of solid particles comprising catalyst and matrix materials is conventional and well known in the art and, therefore, need not be discussed in detail herein.

During the oxygenate conversion reaction, a carbonaceous material. i.e., coke, is deposited on the catalyst. The carbonaceous deposit material has the effect of reducing the number of active sites on the catalyst which thereby affects the extent of the conversion. During the conversion process a portion of the coked catalyst is withdrawn from the reaction zone and regenerated to remove at least a portion of the carbonaceous material and returned to the oxygenate conversion reaction zone. Depending upon the particular catalyst and conversion, it can be desirable to substantially remove the carbonaceous material e.g., to less than 1 wt %, or to only partially regenerate the catalyst, e.g., to from about 2 to 30 wt % carbon. Preferably, the regenerated catalyst will contain about 0 to 20 wt % and, more preferably, from about 0 to 10 wt % carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration. The details concerning the conditions for regeneration are known to those skilled in the art and need not be further disclosed herein.

It was discovered that the butene and heavier material produced in the oxygenate conversion zone, or methanol-to-olefins process, and following separation from the first reaction zone effluent can be converted in a secondary conversion zone to produce additional amounts of ethylene and propylene. It is believed that simply passing a portion of the reactor effluent which comprises methanol to the secondary reaction zone at a higher temperature will not achieve the benefits of the instant invention because the presence of methanol, a polar compound, will inhibit cracking reaction by tying up acid sites on the catalyst. Furthermore, it was surprisingly found that the secondary conversion zone, wherein the butene and heavier material is contacted with a catalyst at conditions effective to convert at least a portion of the butene and heavier materials to ethylene and propylene, favored the production of propylene rather than the smaller molecule, ethylene. The catalyst found to produce this conversion was the same SAPO catalyst employed in the oxygenate conversion zone. The effective conditions at which the additional ethylene and propylene were produced when the butene and heavier were contacted with the catalyst comprised a secondary reaction temperature above about 460° C. Preferably, the secondary reaction temperature comprises a temperature between about 460° C. and about 700° C., and more preferably, the secondary reaction temperature is between about 500° C. and about 700° C., and most preferably, the effective butene cracking reaction temperature is between about 500° C. and about 650° C. Preferably, the effective cracking pressure ranges from about 140 kPa(20 psia) to about 700 kPa (100 psia) and the effective space velocity ranges from about 0.05 $hr^{-1}$ to about 10 $hr^{-1}$. Conversion of the butene produced in the oxygenate conversion was evaluated by measuring the conversion and the selectivity for the production of ethylene in a fixed bed reactor. The fixed bed reactor contained a SAPO-34 catalyst. It was found that conversion of 2-butene at temperatures ranging between 460 and 580° C. resulted in the production of primarily propylene and heavier olefins and initially produced ethylene at a 20% selectivity at short residence times. It was discovered that by increasing reactor temperature over 460° C. and diluting the olefin feed with a nitrogen diluent, the product distribution was shifted toward light olefins. Dilution of the feed with a diluent such as steam appeared to have the same effect on product distribution as dilution with nitrogen. Separate tests with a spray dried catalyst comprising 40% SAPO-34, 40% kaolin clay and 20% Si-Al binder gave the same results as the 100% SAPO-34 powder. It was further surprisingly discovered that there was a significant difference in the conversion of butenes over the SAPO catalyst. The conversion of linear butenes occurred in about the 60 to 70 percent conversion or greater, while conversion of iso-butenes was less than about 15 weight percent. By the removal of the iso-butene by conversion to more valuable products, such as tertiary butyl ethers, the overall profitability of the complex was improved and the size of the butene cracking zone was significantly reduced over schemes processing the entire butene range of material.

The conversion of butylene and heavier material can be accomplished by separating this product fraction from the oxygenate conversion zone effluent and by contacting the butylene and heavier stream or fraction (i.e., $C_4$ plus olefins) with the catalyst from the first reaction zone immediately following regeneration. Ideally, this conversion will take place in a secondary reaction zone between the regeneration and the first reaction zone and the catalyst and the cracked lighter products (ethylene and propylene) will be transferred to the first reaction zone. To effect the cracking reaction favoring light olefins, the secondary reaction zone may be a riser cracking reaction zone with a short residence time to minimize hydrogen transfer reactions which would favor production of paraffins such as ethane and propane. The cracking reactions can also be carried out in a separate fluidized bed containing the oxygenate conversion catalyst. With a separate fluidized bed, the catalyst circulation can be controlled to flow to and from the regenerator at effective catalyst circulation rates which favor the production of ethylene and propylene in the secondary reaction zone and minimize production of the paraffins and methane. When a separate fluidized bed reaction zone is employed as the secondary reaction zone, a product gas stream comprising the cracked products is passed to the oxygenate conversion zone or first reaction zone and catalyst withdrawn from the secondary reaction zone is returned to the regenerator. Because the cracking reaction is a slightly endothermic reaction, some heat of the cracking reaction is provided by the regenerated catalyst. However, an optional butene and heavier preheater may be required to vaporize the feed to the secondary reaction zone when the catalyst circulation rates are very low such as a catalyst to oil (mixed butylene and heavier stream) ratio between about 1 and about 20, In the second reaction zone, preferably the catalyst to oil ratio is less than about 20, and more preferably in the second reaction zone, the catalyst to oil ratio is less than about 10. It is believed that the reaction in the secondary reaction zone over the SAPO catalyst proceeds initially by polymerizing some of the butylene and heavier hydrocarbons in addition to the cracking reactions which, at an effective temperature, favors the production of propylene while also producing ethylene.

A detailed description of processes, including catalyst, processing conditions, and product recovery, for the production of MTBE from iso-butylene and methanol are provided in U.S. Pat. Nos. 2,720,547 and 4,219,678 and in an article at page 35 of the Jun. 25, 1979 edition of Chemical and Engineering News. The preferred process is described in a paper presented at The American Institute of Chemical Engineers, 85th National Meeting on Jun. 4–8, 1978, by F. Obenaus et al. The above references are herein incorporated by reference. Other etherification processes of interest are the production of tertiary amyl methyl ether (TAME) by reacting $C_5$ iso-olefins with methanol, and the production of ethyl tertiary butyl ether (ETBE) by reacting $C_4$ iso-olefins with ethanol, the production of tertiary amyl ethyl ether (TAEE) by reacting $C_5$ iso-olefrns with ethanol, and the production of tertiary hexyl methyl ether (THME) by reacting $C_6$ iso-olefins with methanol. Etherification reactions are carried out in the presence of an acid catalyst such as a sulfonated, macroporous organic ion exchange resin in the liquid phase at temperatures between about 30 and about 100° C.

Generally, the production of ethylene is accompanied by the production of di-olefins such as butadiene. These di-olefins must be removed by any means prior to the production of any ethers or prior to introducing the butene and heavier stream to the butene cracking reactor. Butadiene produced in ethylene plants by the steam cracking process is present in amounts which often justify the recovery of the butadiene by extractive distillation or solvent extraction. U.S. Pat. Nos 4,038,156 and 4,128,457, hereby incorporated by reference, disclose the use of a polar solvent such as acetonitrile to recover butadiene by extractive distillation. When $C_4$ plus olefins are produced in fluid catalytic cracking and methanol to olefins processes, the concentration of butadiene is significantly smaller than produced by steam cracking. Butadiene found in such streams is generally removed by selective hydrogenation in the presence of a solid catalyst comprising nickel and a noble metal such as platinum or palladium or silver as disclosed in U.S. Pat. No. 4,409,410, hereby incorporated by reference.

It is necessary to prevent the buildup of paraffins such as isobutane in the feed to the butene cracking reaction zone. However, butenes and isobutane have close normal boiling points which makes it difficult—by traditional fractionation methods—to reject isobutane from a stream comprising butenes. One method of preventing the buildup of isobutane in the recycle to the butene cracking reaction zone is to withdraw a portion of the butene and heavier fraction as a byproduct heavy olefin stream to be used in motor fuel blending, fuel or for further conversion to petrochemicals. Another method of preventing the buildup of isobutane in the butene cracking reaction zone is to convert the butenes to heavier olefins by a process known as oligomerization. Since the isobutane is not changed in the process, it is more easily fractionated from the oligomerization product. The oligomerization product may be used to produce heavy alcohols or plasticizers, or it may be returned to the butene cracking zone to increase the production of ethylene. Oligomerization reactions of olefinic hydrocarbons having from three to about six carbon atoms are disclosed in U.S. Pat. No. 4,465,885 and U.S. Pat. No. 4,613,719, which are hereby incorporated by reference. The oligomerization reactions are generally carried out in the presence of a solid catalyst comprising copper and phosphate at effective conditions well-known in the art.

DETAILED DESCRIPTION OF THE DRAWINGS

The process of the present invention is hereinafter described with reference to the drawing which illustrates various aspects of the present invention. It is to be understood that no limitation to the scope of the claims which follow is intended by the following description. Those skilled in the art will recognize that these process flow diagrams have been simplified by the elimination of many necessary pieces of process equipment including valves, some heat exchangers, process control systems, pumps, fractionation column overhead and reboiler systems, etc. It may also be readily discerned that the process flow presented in the drawings may be modified in many aspects without departing from the basic overall concept of the invention.

Referring to the figure, a feedstream in line 10 is passed to an olefin production zone 101 to catalytically or thermally convert the feedstream into an olefinic product stream in line 14 comprising olefinic compounds containing from 2 to about 12 carbon atoms per molecule. The olefin conversion reaction to olefins is typically conducted in the presence of steam. The olefinic product stream in line 14 is passed via lines 14 and 16 to a olefin separation zone 112 for the separation of the olefinic product stream in the conventional manner into a light ends stream in line 18, an ethylene stream in line 20, a propylene stream in line 22. In olefin separation zone 112, the olefinic product stream is further separated to provide a butylene and heavier stream (or $C_4$ plus olefin stream) in line 30 which comprises butylenes, pentenes, and hexenes. A reject stream comprising very heavy olefins such as $C_8$ and heavier olefins and aromatic hydrocarbons is withdrawn in line 28. This reject stream may be used for fuel or passed to downstream processing for further recovery. The butylene and heavier stream in line 30 may also comprise dienes, such as butadienes. The butylene and heavier stream is passed in lines 30, 26 and 38 to a selective hydrogenation reaction zone 118 wherein the butylene and heavier stream is contacted with a selective hydrogenation catalyst in the presence of hydrogen supplied via line 66 to convert the dienes to mono-olefins and produce a mixed mono-olefin stream in line 72. The mixed mono-olefin product stream is passed to an iso-olefin removal zone incorporating a fractionation step or a combination of a reaction step and a fractionation step for the removal of iso-olefins from the mono-olefin product stream. In one embodiment, the iso-olefin removal zone comprises passing the mono-olefin product stream in line 72 to an olefin conversion zone 102 wherein an an oxygen-containing compound, or oxygenate such as methanol, ethanol, or water in line 12 is combined with the mono-olefin product stream in the presence of an acid catalyst to produce a conversion product stream in line 68. In one aspect of the invention the olefin conversion zone 102 comprises an etherification zone and the conversion product stream comprises an ether product stream. In the etherification zone, which contains an acid catalyst, the mixed mono-olefin stream is contacted with at least a stoichiometric amount of an alcohol such as ethanol or methanol in the conventional manner to produce the ether product stream. The conversion product stream comprises an oxygenate such as an ether or an alcohol. Ethers produced in olefin conversion zone 102 can include methyl or ethel tertiary butyl ether, or similar ethers derived from iso-pentenes, or ethers derived from iso-hexenes to the extent these iso-olefins are present in the mixed mono-olefin stream in line 72. Similarly, the conversion product stream in line 68 may comprise alcohols such as tertiary butyl alcohol and/or similar alcohols produced from iso-pentenes and iso-hexenes. The alcohols or ethers are removed from the conversion product stream in line 68 by passing the conversion product stream to an oxygenate separation zone 116 to provide an oxygenate product stream in line 70 and a net butylene and heavier stream comprising a reduced amount of iso-olefins in line 40 relative to the amount of iso-olefins in the mixed mono-olefin stream in line 72. A portion of the net butylene and heavier stream in line 40 is passed in lines 42 and 54 to a butylene cracking zone 104 wherein the mono-olefins at effective conditions are contacted with a small pore selective catalyst for the conversion of the mono-olefins to produce additional amounts of ethylene and propylene. A light olefin product stream comprising the additional amounts of ethylene and propylene in line 58 is withdrawn from the butylene cracking zone 104 and passed to the olefin separation zone 112 via lines 58 and 16. During the butylene cracking reaction within the butylene cracking zone 104, the selective catalyst rapidly deactivates by the formation of coke or carbon on the butylene cracking catalyst which produces a deactivated cracking catalyst. A portion of the deactivated cracking catalyst is withdrawn from the butylene cracking zone 104 and passed via line 56 to a regenerator zone 110 wherein deactivated butylene cracking catalyst, containing from about 3 to about 20 weight percent coke, is regenerated by contacting the deactivated cracking catalyst with an oxygen-containing stream in line 62 to produce a re-generated catalyst. Typically the oxygen-containing stream comprises from about 1 to about 3 mol-percent oxygen. A portion of the regenerated catalyst is withdrawn from the regeneration zone 110 in line 52 and is returned to the butylene cracking zone 104 via line 52 and line 54 where it is admixed with the mono-olefin product stream in line 54. The butylene cracking reaction is carried out in the presence of a purge stream comprising steam or inert diluent such as nitrogen, methane, or light paraffin hydrocarbon, containing 2 to 4 hydrocarbons. In order to prevent the buildup of light paraffins in the butylene cracking zone 104, at least a portion of the net butylene and heavier stream in line 40 is withdrawn as a drag stream in line 44. The drag stream may be fractionated in a conventional manner (not shown) to separate the paraffin portion from the olefin portion, wherein the olefin portion is returned to the butylene cracking zone, or the drag stream 44 is passed to an oligomerization zone 106 wherein the low carbon number, normal olefins, such as butene-1 and butene-2 combine to form heavier normal olefins, having about 8 carbon atoms per molecule to produce an oligomerization effluent stream in line 48. The oligomerization effluent stream in line 48 is passed to an oligomerization separation zone 108 to provide a light paraffin stream, comprising butanes in line 64 and a heavy olefin stream in line 50. The heavy olefin stream may be withdrawn in line 50' as a raw material for plasticizer and alcohol production, or a portion of the heavy olefin stream in line 50 may be returned to the butylene cracking zone via lines 50 and 54 to produce additional amounts of ethylene and propylene.

In an alternate embodiment, a portion of the butylene and heavier stream is processed in an alternate or additional di-olefin removal zone. In this alternative the di-olefin removal zone comprises a butadiene extraction zone which operates at effective conditions and employs a selective solvent to extract the butadiene from the butylene and heavier stream to produce a raffinate stream essentially free of di-olefins. According to this alternate operation, the butylene and heavier stream in line 30 is passed via lines 30 and 36 to a butadiene extraction unit 114 wherein di-oelfins are extracted from the butylene and heavier stream in the conventional manner and a butadiene extract stream is withdrawn in line 32. The raffinate stream comprising mono-olefins and paraffins in line 34, is passed to the selective hydrogenation reaction zone 118 via lines 34 and 38.

EXAMPLES

The following examples are only used to illustrate the present invention and are not meant to be limiting.

Example I

Generally, the conversion of oxygenates to light olefuis, specifically ethylene, can be improved by increasing the temperature at which the reaction takes place. However, as temperature is increased, the catalyst life drops significantly. To illustrate the degradation in catalyst activity, three oxygenate conversion pilot plant runs were conducted using a spray-dried metal aluminophosphate catalyst comprising 40% SAPO-34, 40% kaolin clay and 20% Si—Al binder. The catalyst was loaded into a 2.2 cm (⅞ inch) ID porcelain-lined, stainless steel reactor and placed in a three-zone bronze block furnace. The reactor was heated to 435° C. for Run A, 455° C. for Run B, and 475° C. for Run C under an $N_2$ purge at 138 kPa (5 psig). These conditions were held for 1 hour in each run to pretreat the catalyst. The $N_2$ flow was stopped and a methanol/water mixture (80/20 by weight) was introduced at 1 hr$^{-1}$ MeOH WHSV (weight hourly space velocity based on methanol) and continued until the reactor effluent contained greater than 50% MeOH and DME. Table 1 summarizes the time on stream and product selectivities at the point where the overall conversion was 99% for each run. It can be seen by comparing run A to run C that increasing reaction temperature by about 40° C. increases the ethylene/propylene product ratio from about 1.5 to about 2.0, but increasing reaction temperature also decreases the catalyst life by about 50%. At lower reactor temperatures, larger amounts of butene and heavier compounds, primarily $C_4$–$C_{12}$ olefins and some small amounts of aromatic hydrocarbons are produced.

TABLE 1

SUMMARY OF OXYGENATE CONVERSION
SELECTIVITIES FOR SAPO-34
WITH INCREASING REACTOR TEMPERATURE

| RUN | A | B | C |
| --- | --- | --- | --- |
| Inlet Temp (° C.) | 435 | 455 | 475 |
| Pressure (kPa) | 138 | 138 | 138 |
| MeOH WHSV (hr$^{-1}$) | 1.0 | 1.0 | 1.0 |
| Catalyst Life (hr at >99% Conv) | 4.3 | 3.3 | 2.3 |
| Selectivities at 99% Conversion (mole %) | | | |
| $C_1$ | 3.3 | 4.7 | 7.7 |

TABLE 1-continued

SUMMARY OF OXYGENATE CONVERSION
SELECTIVITIES FOR SAPO-34
WITH INCREASING REACTOR TEMPERATURE

| RUN | A | B | C |
|---|---|---|---|
| $C_2$ | 0.6 | 0.6 | 0.8 |
| $C_2^-$ | 50.3 | 52.4 | 53.7 |
| $C_3$ | 0.4 | 0.4 | 0.5 |
| $C_3^-$ | 33.5 | 30.8 | 27.0 |
| $C_4S$ | 9.0 | 7.9 | 6.9 |
| $C_{5+}S$ | 2.0 | 3.1 | 3.2 |
| $C_2^-/C_3^-$ Ratio | 1.50 | 1.70 | 1.99 |

Example II

By converting the butene and heavier compounds over the same catalyst at effective conditions, it was proposed that improved ethylene yields would result. The conversion of butenes over an aluminophosphate catalyst was evaluated with a catalyst containing about 40 weight percent SAPO-34 and a binder for a series of reactor temperatures to simulate riser reactor operation in a fixed bed reactor. Approximately 20 g of catalyst were loaded into a 2.2 cm (⅞ inch) ID porcelain-lined, stainless steel reactor and placed in a 3-zone bronze block furnace. The reactor was heated to temperatures between 460 and 580° C. and purged with nitrogen for approximately 1 hour to precondition the catalyst. The nitrogen flow was stopped and 2-butene was introduced at a rate of about 0.5 hr$^{-1}$ WHSV on catalyst for a period of about 5 hours.

According to the above procedure, the reactor was filled with the SAPO-34 containing catalyst and was heated to a temperature of 460° C. Following 1 hour of purging with nitrogen, vaporized 2-butene was introduced to the reactor at a rate of about 0.5 WHSV on catalyst. The conversion of the 2-butene gradually decreased from an initial value of 66 percent to a value near the end of the run of about 44 percent at about 4.5 hours on stream. The selectivity to ethylene began at about 7% and decreased to about 6% over the same period. The selectivity to propylene began at about 25% and increased to about 30% over the same period.

Example III

The procedure of Example II was repeated at a reactor temperature of about 580° C. At 580° C., the initial $C_4$ olefin conversion was 75% and decreased more rapidly than in Example II, reaching a value of about 30% after about 4.5 hours on stream. The selectivity to ethylene initially was about 20% and decreased to about 8% after about 4.5 hours on stream. The selectivity to methane initially was about 10% and increased to about 17% after about 4.5 hours on stream. The selectivity to propylene initially was about 35% and decreased to about 32% after about 4.5 hours on stream.

Example IV

The procedure of Example II was repeated at a reactor temperature of about 580° C., and after heating and purging the reactor with nitrogen for about 1 hour, the 2-butene vapor was introduced at about 75% dilution with nitrogen. The conversion of $C_4$'s was about 70% initially and decreased to about 5% after about 4.5 hours on stream. The selectivity to ethylene initially was about 22% and decreased to about 12 percent after about 4.5 hours on stream. The selectivity to methane initially was about 3 percent and increased to about 12% after about 4.5 hours on stream. The selectivity to propylene was 55% initially and decreased to about 45% after about 4.5 hours on stream.

We claim:

1. A process for producing ethylene and propylene comprising:
   a) passing a feedstream to an olefin production zone and therein producing an olefinic product stream comprising ethylene, propylene, and butylene;
   b) passing the olefinic product stream to an olefin separation zone to provide an ethylene product stream, a propylene product stream, and a $C_4$ plus olefin stream;
   c) passing the $C_4$ plus olefin stream comprising normal and iso-olefins, and di-olefins to a di-olefin removal zone to provide a mixed mono-olefin stream comprising normal olefins and iso-olefins;
   d) converting at least a portion of the mixed mono-olefin stream in an olefin conversion zone containing an acid catalyst selective for the conversion of iso-olefins in the presence of an oxygen-containing compound to provide a conversion product stream comprising oxygenates and normal olefins;
   e) passing the conversion product stream to an oxygenate separation zone to separate oxygenates from the normal olefins and produce a net butylene stream;
   f) passing at least a portion of the net butylene stream to a butylene cracking zone and therein contacting the net butylene stream with a small pore selective catalyst for the cracking of the normal olefins to produce a light olefin stream comprising additional amounts of ethylene and propylene; and,
   g) recovering the additional amounts of ethylene and propylene.

2. The process of claim 1 wherein the small pore selective catalyst for cracking of normal olefins is selected from the group consisting of ferrierite and non-zeolitic molecular sieves.

3. The process of claim 1 wherein the small pore selective catalyst comprises a non-zeolitic molecular sieve catalyst having an effective small pore size and an empirical chemical composition, on an anhydrous basis, expressed by the empirical formula:

$(EL_xAl_yP_z)O_2$ where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1.

4. A process for producing ethylene and propylene comprising:
   a) passing a feedstream to an olefin production zone and therein producing an olefinic product stream comprising ethylene, propylene, and butylene and heavier olefins;
   b) passing the olefinic product stream to an olefin separation zone to provide an ethylene product stream, a propylene product stream, a mixed butylene and heavier stream, and a reject stream;
   c) passing the mixed butylene and heavier stream comprising normal olefins, iso-olefins, paraffins, and di-olefins to a di-olefin removal zone to provide a mixed mono-olefin stream comprising normal olefins, iso-olefins, and paraffins;

d) converting at least a portion of the mixed mono-olefin stream in an olefin conversion zone containing an acid catalyst selective for the conversion of iso-olefins in the presence of at least a stoichiometric amount of an oxygen-containing compound to provide a conversion product stream comprising oxygenates, normal olefins, and paraffins;

e) passing the conversion product stream to an oxygenate separation zone to separate oxygenates from the normal olefins and produce a net butylene stream;

f) passing at least a portion of the net butylene stream to a butylene cracking zone and therein contacting the net butylene stream with a small pore selective catalyst for the cracking of the normal olefins to produce a light olefin stream comprising additional amounts of ethylene and propylene; and, g) recovering the additional amounts of ethylene and propylene.

5. The process of claim 4 further comprising passing a portion of the net butylene stream to an oligomerization zone to produce an oligomerization effluent stream and separating the oligomerization effluent stream to provide a paraffin stream comprising butanes and to provide a heavy olefin stream.

6. The process of claim 5 further comprising passing a portion of the heavy olefin stream to the butylene cracking zone.

7. The process of the claim 4 wherein the olefin production zone comprises a process selected from a group consisting of catalytic cracking, pyrolysis, and methanol-to-olefins conversion.

8. The process of claim 4 wherein the olefin conversion zone comprises a process for the etherification of iso-olefin with an oxygen-containing compound selected from the group consisting of methanol, ethanol, propanol, and mixtures thereof to produce oxygenates comprising tertiary alkyl ethers.

9. The process of claim 8 wherein the tertiary alkyl ethers comprise methyl tertiary butyl ether or ethyl tertiary butyl ether.

10. The process of claim 4 wherein the olefin conversion zone comprises a process for the hydration of iso-olefin with an oxygenate comprising water to produce an alcohol product.

11. The process of claim 10 wherein the alcohol product comprises tertiary butyl alcohol.

12. The process of claim 4 wherein the feedstream is selected from the group consisting of natural gas, liquefied petroleum gas, naphtha, and gas oil and the olefin-production zone comprises a pyrolysis process.

13. The process of claim 4 wherein the olefin production zone comprises a fluid catalytic cracking unit and the feedstream comprises a heavy gas oil.

14. The process of the claim 4 wherein the olefin production zone comprises a methanol-to-olefin process and the feedstream comprises an oxygenate selected from the group consisting of alcohols, ethers, ketones, and mixtures thereof.

15. The process of claim 4 wherein the small pore selective catalyst for cracking of normal olefins is selected from the group consisting of ferrierite and non-zeolitic molecular sieves.

16. The process of claim 4 wherein the small pore selective catalyst comprises an effective pore size less than about 5.0 Angstroms.

17. The process of claim 4 wherein the small pore selective catalyst is selected from the group consisting of SAPO-34, SAPO 17, SAPO 11 and mixtures thereof.

18. The process of claim 4 wherein the small pore selective catalyst comprises a non-zeolitic catalyst having an effective small pore size and an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1.

19. A process for producing ethylene and propylene comprising:

a) passing a feedstream comprising an oxygenate selected from the group consisting of methanol, dimethyl ether, ethanol, and mixtures thereof to an olefin production zone containing a non-zeolitic catalyst having an effective small pore size and an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1, and in said olefin production zone producing an olefinic product stream comprising ethylene, propylene, and butylene and heavier olefins;

b) passing the olefinic product stream to an olefin separation zone to provide an ethylene product stream, a propylene product stream, a mixed butylene and heavier stream, and a reject stream;

c) passing the mixed butylene and heavier stream comprising mono-olefins and di-olefins to a selective hydrogenation zone and therein contacting the mixed butylene and heavier stream with a hydrogenation catalyst in the presence of hydrogen to convert the di-olefins to mono-olefins and to provide a mixed mono-olefin stream comprising normal olefins, iso-olefins, and paraffins;

d) passing the mixed mono-olefin stream to an etherification zone containing an acid catalyst, and in the presence of at least a stoichiometric amount of an alcohol, converting the iso-olefins to provide an ether product stream essentially free of iso-olefins comprising oxygenates, normal olefins, and paraffins;

e) passing the ether product stream to an oxygenate separation zone to separate oxygenates from the normal olefins and produce a net butylene stream;

f) passing at least a portion of the net butylene stream at effective cracking conditions to a butylene cracking zone containing a small pore catalyst selective for the conversion of linear mono-olefins to light olefins and therein contacting the net butylene stream with said catalyst to produce a light olefin stream comprising additional amounts of ethylene and propylene; and, g) recovering the additional amounts of ethylene and propylene.

20. The process of claim 19 wherein the effective small pore size of the non-zeolitic catalyst of step (a) comprises less than about 5 Angstroms.

21. The process of claim 19 wherein the small pore catalyst selective for the conversion of linear mono-olefins to light olefins is selected from the group consisting of SAPO-34, SAPO-17, SAPO-11 and mixtures thereof.

22. The process of claim 19 wherein the ether product comprises an alkyl tertiary butyl ether.

23. The process of claim 19 wherein effective cracking conditions include an effective cracking temperature ranging between about 460° C. and about 700° C. (about 860° F. and about 1292° F.) and an effective cracking pressure ranging from about 140 kPa (20 psia) to about 700 kPa (100 psia) and a space velocity ranging from about 0.05 hr$^{-1}$ to about 10 hr$^{-1}$.

24. The process of claim 19 wherein the small pore selective catalyst for the conversion of linear mono-olefins to light olefins comprises a non-zeolitic catalyst having an effective small pore size and an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1.

25. The process of claim 19 wherein the small pore selective catalyst for the conversion of linear mono-olefins to light olefins is selected from the group consisting of ferrierite and non-zeolitic molecular sieves.

* * * * *